United States Patent [19]

Mattson et al.

[11] Patent Number: 5,475,729

[45] Date of Patent: Dec. 12, 1995

[54] X-RAY REFERENCE CHANNEL AND X-RAY CONTROL CIRCUIT FOR RING TUBE CT SCANNERS

[75] Inventors: Rodney A. Mattson, Mentor; Theodore A. Resnick, Beachwood, both of Ohio

[73] Assignee: Picker International, Inc., Highland Heights, Ohio

[21] Appl. No.: 224,958

[22] Filed: Apr. 8, 1994

[51] Int. Cl.⁶ .................................................. H01J 35/04
[52] U.S. Cl. .......................... 378/135; 378/108; 378/134; 378/138
[58] Field of Search .................................... 378/135, 134, 378/136, 137, 138, 119, 121, 97, 108, 110, 109, 111, 112, 113

[56] References Cited

U.S. PATENT DOCUMENTS

| | | | |
|---|---|---|---|
| 2,825,816 | 3/1958 | Rogers | 378/110 X |
| 4,122,346 | 10/1978 | Enge | 250/398 |
| 4,135,095 | 1/1979 | Watanabe | 250/445 T |
| 4,227,088 | 10/1980 | Maydan et al. | 250/445 T |
| 4,274,005 | 6/1981 | Yamamura et al. | 378/137 X |
| 4,300,051 | 11/1981 | Little | 250/445 T |
| 4,368,535 | 1/1983 | Baumann | 378/15 |
| 4,521,900 | 6/1985 | Rand | 378/137 |
| 4,639,943 | 1/1987 | Heinze et al. | 378/112 X |
| 4,739,168 | 4/1988 | Aoki | 378/167 X |
| 4,935,945 | 6/1990 | Mochizuki et al. | 378/97 |
| 5,012,498 | 4/1991 | Cuzin et al. | 378/110 X |
| 5,081,663 | 1/1992 | Gerlach et al. | 378/162 X |
| 5,103,469 | 4/1992 | Tanaka | 378/16 |
| 5,125,012 | 6/1992 | Schittenhelm | 378/10 |
| 5,179,583 | 1/1993 | Oikawa | 378/135 |
| 5,195,112 | 3/1993 | Vincent et al. | 378/137 X |
| 5,200,985 | 4/1993 | Miller | 378/136 X |
| 5,235,191 | 8/1993 | Miller | 250/486.1 |
| 5,241,577 | 8/1993 | Burke et al. | 378/135 |
| 5,291,538 | 3/1994 | Burke et al. | 378/136 X |
| 5,305,363 | 4/1994 | Burke et al. | 378/136 X |

FOREIGN PATENT DOCUMENTS

| | | |
|---|---|---|
| 0377534A1 | 7/1990 | European Pat. Off. . |
| 0564292 | 8/1993 | European Pat. Off. . |
| 0597725 | 5/1994 | European Pat. Off. . |
| 2613620 | 10/1977 | Germany ............... 378/108 |
| 3635950 | 4/1987 | Germany . |
| 0124997 | 9/1988 | Japan ............... 378/108 |
| 2034149 | 5/1980 | United Kingdom . |
| 2069129 | 8/1981 | United Kingdom . |

OTHER PUBLICATIONS

"Scintillating Optical Fibers", Bicron Corporation Advertising Brochure, pp. 1–6 No date.

*Primary Examiner*—David P. Porta
*Attorney, Agent, or Firm*—Fay, Sharpe, Beall, Fagan, Minnich & McKee

[57] ABSTRACT

A toroidal x-ray tube (I) is supported and selectively positioned by a gantry (II). The x-ray tube includes a toroidal housing (A) in which a rotor (30) is rotatably mounted. One or more cathodes (C) are mounted on the rotor for generating an electron beam which strikes an anode (B) to generate a beam of x-rays which passes through a window (20) and strikes an annular ring of detectors (160). A grid bias control circuit (100) selectively applies a continuously adjustable bias to a grid (36) for regulating the electron current, hence the intensity of the x-ray beam. A scintillating optical fiber (110) extends around the exterior of the window. The scintillation optical fiber includes fluorescent dopant (116) which convert a very small fraction of the x-rays into optical light which is transmitted along the fibers to an opto-electric transducer (118). The opto-electric transducer is connected with the grid bias control circuit. The opto-electrical transducer (118) can also be connected with an intensity compensator (162) for adjusting the signals from the detector ring before they are reconstructed (164) into an image representation.

25 Claims, 4 Drawing Sheets

X-RAY REFERENCE CHANNEL AND X-RAY CONTROL CIRCUIT FOR RING TUBE CT SCANNERS

BACKGROUND OF THE INVENTION

The present invention pertains to the art of detecting and controlling the intensity x-ray fluence. It finds particular application in conjunction with annular x-ray tubes for CT scanners and will be described with particular reference thereto. However, it is to be appreciated that the present invention will also find application in conjunction with the generation of radiation for other applications.

Typically, a patient is positioned in a supine position on a horizontal couch through a central bore of a CT scanner. An x-ray tube is mounted on a rotatable gantry portion and rotated around the patient at a high rate of speed. For faster scans, the x-ray tube is rotated more rapidly. However, rotating the x-ray more rapidly decreases the net radiation per image. As CT scanners have become faster, larger x-ray tubes have been developed which generate more radiation per unit time to maintain the desired radiation dose at higher speeds. Larger tubes, of course, cause high inertial forces.

High performance x-ray tubes for CT scanners and the like commonly include a stationary cathode and a rotating anode disk, both enclosed within an evacuated housing. As more intense x-ray beams are generated, there is more heating of the anode disk. In order to provide sufficient time for the anode disk to cool by radiating heat through the vacuum to surrounding fluids, x-ray tubes with progressively larger anode disks have been built.

The larger anode disk requires a larger x-ray tube which does not readily fit in the small confined space of an existing CT scanner gantry. Particularly in a fourth generation scanner, incorporating a larger x-ray tube and heavier duty support structure requires moving the radiation detectors to a larger diameter. A longer radiation path between the x-ray tube and the detectors would require that the detectors would be physically larger to subtend the required solid angle. Larger detectors would be more expensive. Not only is a larger x-ray tube required, larger heat exchange structures are required to remove the larger amount of heat which is generated.

In an x-ray tube with a fixed anode and a fixed cathode or with a rotating anode and fixed cathode, accurate control of the radiation dose delivered to the patient was relatively simple. Because the quality of the reconstructed image is dependent upon the number of x-ray photons that are captured by the radiation detector, accurate control of the number of x-ray photons generated is important for good CT images. In order to control the amount of radiation generated, the x-ray tube current is typically monitored and the cathode current is controlled accordingly. Typically, the cathode is fixed at a high negative voltage relative to the housing and the anode similarly fixed to a high positive voltage. Control of the tube current passing between the anode and the cathode (actually an electron flow cathode to anode) is typically done by controlling the temperature of a directly heated cathode filament. More specifically, the electron density from the filament surface is a function of the temperature, the applied anode/cathode voltage, the geometry of the cathode structure, and the distance from the cathode to the anode. The filament temperature is traditionally controlled by controlling a filament heating current.

Rather than rotating a single x-ray tube around the subject, others have proposed using a switchable array of x-ray tubes, e.g. five or six x-ray tubes in a ring around the subject. See, for example, U.S. Pat. No. 4,274,005 to Yamamura. However, unless the tubes rotate only limited data is generated and only limited image resolution is achieved. If multiple x-ray tubes are rotated, similar mechanical problems are encountered trying to move all the tubes quickly and remove all of the heat.

Still others have proposed constructing an essentially bell-shaped, evacuated x-ray tube envelope with a mouth that is sufficiently large that the patient can be received a limited distance in the well of the tube. See, for example, U.S. Pat. No. 4,122,346 issued Oct. 24, 1978 to Enge or U.S. Pat. No. 4,135,095 issued Jan. 16, 1979 to Watanabe. An x-ray beam source is disposed at the apex of the bell to generate an electron beam which impinges on an anode ring at the mouth to the bell. Electronics are provided for scanning the x-ray beam around the evacuated bell-shaped envelope. One problem with this design is that it is only capable of scanning about 270°.

Still others have proposed open bore x-ray tubes. See, for example, U.S. Pat. No. 5,125,012 issued Jun. 23, 1992 to Schittenhelm and U.S. Pat. No. 5,179,583 issued Jan. 12, 1993 to Oikawa. These large diameter tubes are constructed analogous to conventional x-ray tubes with a glass housing and a sealed vacuum chamber. Such tubes are expensive to fabricate and are expensive to repair or rebuild in case of tube failure.

One problem with rotating cathode x-ray tubes resides in the difficulty of monitoring the x-ray tube current. The tube current is generally more easily measured at the anode portion of the tube. Measuring the x-ray tube current with an end grounded anode is difficult. Measuring the x-ray tube filament current on the rotating cathode side within the vacuum is also difficult because the filament is rotating and there is no direct means of measurement.

Another problem is controlling the cathode filament temperature accurately. The filament current is supplied to the rotating cathode by a transformer, capacitive coupling, or the like across a vacuum. Any wobble or variation in the gap between transformer or capacitive elements tends to vary the x-ray tube current. This causes difficulties in controlling the filament current in the rotating cathode assembly.

The present invention contemplates a new and improved toroidal x-ray tube and toroidal x-ray tube CT scanner which provides for improved x-ray photon intensity measurement and control.

SUMMARY OF THE INVENTION

A large diameter toroidal housing is provided. An anode target is disposed in the housing with an annular window for directing x-rays toward a central axis of the annular housing. An annular rotor is rotatably received in the toroidal housing. At least one cathode is mounted on the rotor for generating an electron beam which strikes the anode target. A means is provided for rotating the rotor and the cathode such that the electron beam is rotated around the anode.

In accordance with one aspect of the present invention, a stationary, annular radiation intensity detector is mounted around the annular window.

In accordance with a more limited aspect of the present invention, the stationary radiation detector includes a ring of scintillation optic fiber. The scintillation optic fiber includes scintillators which convert a very small fraction of the incident radiation into light which is trapped in and passed along the optical fiber to a light intensity detector.

In accordance with an alternate embodiment of the present invention, an annular ionization chamber or other structure for monitoring the intensity of the radiation passing through the window is provided.

In accordance with another aspect of the present invention, a bias control circuit adjusts a bias on an x-ray beam focusing assembly in order to control the tube current, hence the x-ray photon intensity.

In accordance with more limited aspect of the present invention, bias potential is communicated between the stationary housing and the rotating cathode across an annular transformer assembly.

In accordance with another aspect of the present invention, the bias control circuit is sealed in a vacuum tight can and mounted to the rotor within the evacuated interior of the toroidal housing.

In accordance with another aspect of the present invention, a plurality of cathodes are mounted on the rotor. A resonance circuit is connected with each of the cathodes. One of the cathodes which is to be active is selected by adjusting the frequency of the cathode filament current such that only the resonance circuit of the selected cathode passes the filament current and the resonance circuits of the other cathodes block the filament current.

In accordance with another aspect of the present invention, the toroidal x-ray tube is incorporated into a CT scanner.

One advantage of the present invention is that it monitors actual x-ray intensity with a very fast response time without introducing extraneous noise into the x-ray receiving subsystem or degrading resultant CT images.

Another advantage of the present invention is that it yields improved images by providing for real time adjustments to the image reconstruction algorithm to compensate for any x-ray intensity fluctuations.

Another advantage of the present invention is that the x-ray tube current is accurately controlled.

Another advantage of the present invention is that it enables the tube current to be controlled relatively independent of the filament current.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE PREFERRED EMBODIMENTS

Figure 1:
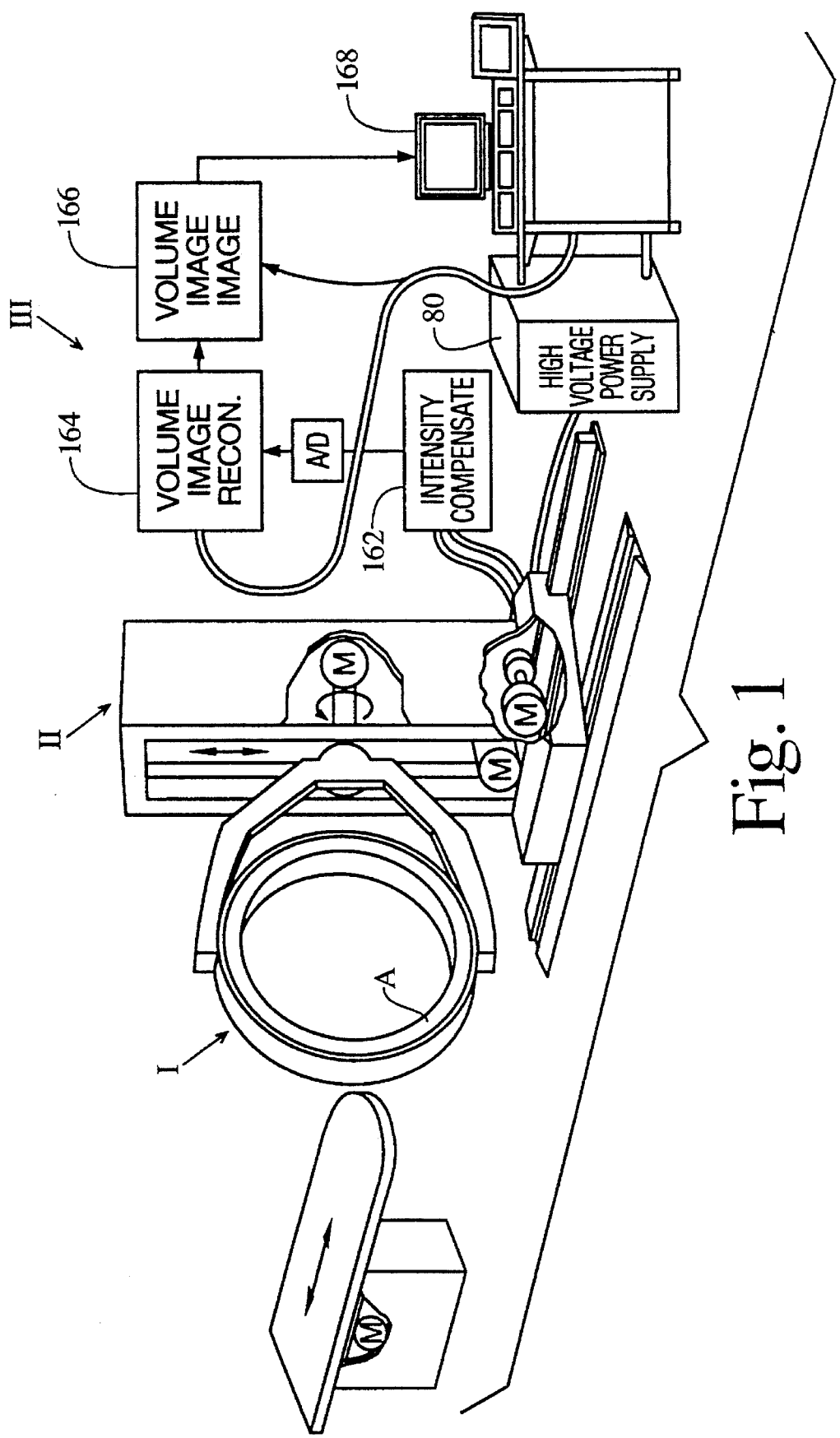
FIG. 1 is a perspective view of a CT scanner system in accordance with the present invention.

With reference to FIG. 1, a CT scanner includes a toroidal ring x-ray tube I which is mounted to a gantry or mounting assembly II. An electronics section III a high voltage power supply, a filament current supply, a tube current control and circuitry for providing operating power and control signals to the gantry. The electronic section further receives data from the gantry and reconstructs the received data into an electronic image representation.

Figure 2:
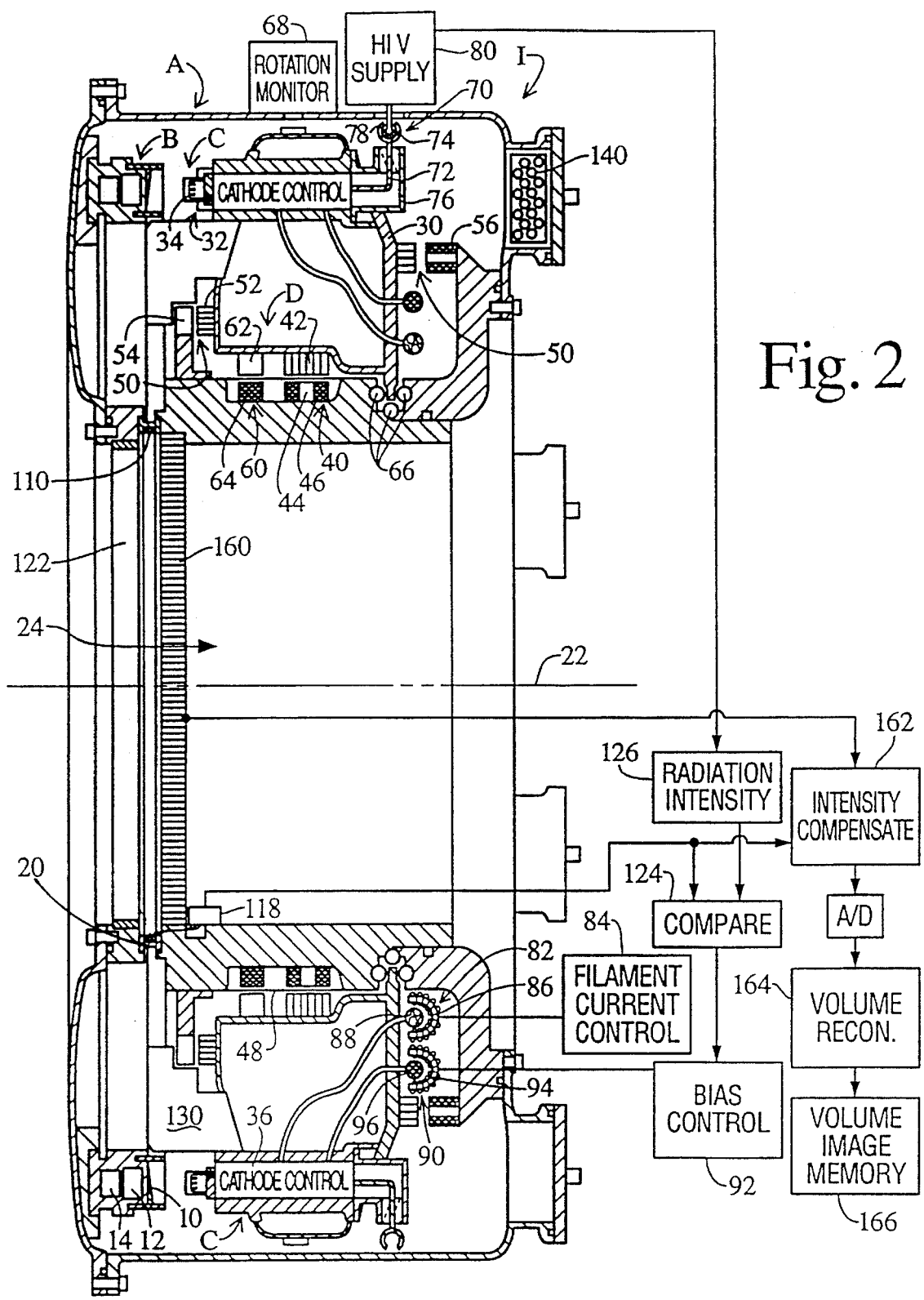
FIG. 2 is a cross-sectional view of the toroidal, rotating cathode x-ray tube of FIG. 1.

With reference to FIG. 2, the ring tube I includes a toroidal housing A which defines a large, generally donut-shaped interior volume. An anode B is mounted within the toroidal housing interior volume and extends circumferentially therearound. A cathode means C is disposed within the toroidal housing interior space for generating at least one beam of electrons. A means D selectively rotates the electron beam around the anode B.

More specifically, the anode B is a tungsten ring having a tungsten face 10 upon which the electron beam impinges. The anode assembly defines an annular anode adjacent cooling fluid path or channel 12 in intimate thermal communication with the anode face, specifically along an opposite surface of the anode. Optionally, the anode can have internal passages, fins, and the like to promote thermal communication with the cooling fluid.

A window means 20 is mounted in the housing A in radial alignment with the tungsten face 10 of the target anode. The window is positioned such that x-rays generated by interaction of the electron beam and the tungsten target anode 10 are directed transverse to a central axis 22 of a bore 24 of the toroidal tube.

An annular ring or rotor 30 extends around an interior of the toroidal housing A. The rotor supports a corresponding plurality of cathode assemblies C. Each of the cathode assemblies includes a cathode cup 32 which contains a filament or other electron source 34 and a cathode control circuit 36. The filament 34 and the anode 10 are maintained at a high relative voltage relative to each other, e.g. 150 kV. The housing A and the rotor 30 are maintained at a common potential, preferably ground potential. In the preferred embodiment, the anode is also maintained at ground potential and the cathode cup is insulated from the rotor 30 and maintained at about −150 kV. Alternately, the anode may be maintained at approximately +75 kV and the cathode at about −75 kV relative to ground.

The rotor 30 is rotatably supported within the housing A on a bearing means 40, a magnetic levitation bearing in the embodiment of FIG. 2. The magnetic levitation bearing includes rings of silicon steel 42, which are stable within the vacuum, mounted along an inner radius of the rotor 30. Passive and active elements including permanent magnets 44 and electromagnets 46 are disposed closely adjacent the rings 42 of silicon steel. The housing A includes a magnetic window 48 which separates the vacuum region from the electromagnets 46. The magnetic window permits magnetic flux to pass but prevents epoxy or other polymers commonly used in coils from outgassing into the vacuum region.

To maintain the alignment of the rotor ring a pair of oppositely disposed magnetic levitation bearings 50 are mounted on opposite sides of the rotor. Each has rings of silicon steel 52 and permanent magnets 54 to provide opposing forces on the rotor. The magnetic levitation bearing on one side also has electromagnetic coils 56 to adjust the relative opposing forces. Position sensors, not shown but conventional in the art, are provided for controlling the electromagnetic coils to maintain the position of the rotor 30 precisely.

The rotating means D includes a large diameter brushless motor 60. A rotor 62, preferably of permanent magnets, is mounted to the rotor 30 within the vacuum region. A stator 64 including electromagnetic windings, is positioned directly opposite the rotor 62 but across the magnetic window 48 outside of the vacuum region. Mechanical roller bearings 66, normally out of contact with the rotor, are provided to support the rotor 30 in the event the magnetic levitation system should fail. The mechanical roller bearings prevent the rotor 30 from interacting directly with the stationary housing A and other associated structures. An angular position monitor 68 monitors the angular position of the rotation of the rotor 30, hence the angular position of the cathode assemblies and the apices of the x-ray beams precisely.

Each of the cathode assemblies C include insulation for insulating the cathode assembly from the rotor 30. An electrical conductor 72 extends from one end of the filament 34 to a first electrical power transfer means 70 for transferring the cathode biasing potential from the stationary housing A to the cathode assemblies. The first power transfer means includes a toroidal ring 74 which is supported by but insulated from the rotor 30 by a series of mounting brackets 76. A hot cathode filament 78 is connected with a high voltage supply system 80. The hot cathode filament 78 is preferably of a lower work function type. The toroidal channel 74 which partially surrounds the hot cathode filament 78 is maintained near the potential of the hot filament by the transfer of electrons therebetween.

A second power transfer means 82 transfers a filament current to the cathode assemblies. The second power transfer means includes a filament control circuit 84, a horse-shoe shaped primary coil 86, and an annular secondary coil 88.

A third power transfer means 90 transfers a bias potential for adjustably controlling a cathode bias. The third power transfer means includes a first bias control circuit 92 off the rotor for designating a selected bias. A horse-shoe shaped primary 94 transfers the bias potential to an annular secondary 96.

Figure 3:
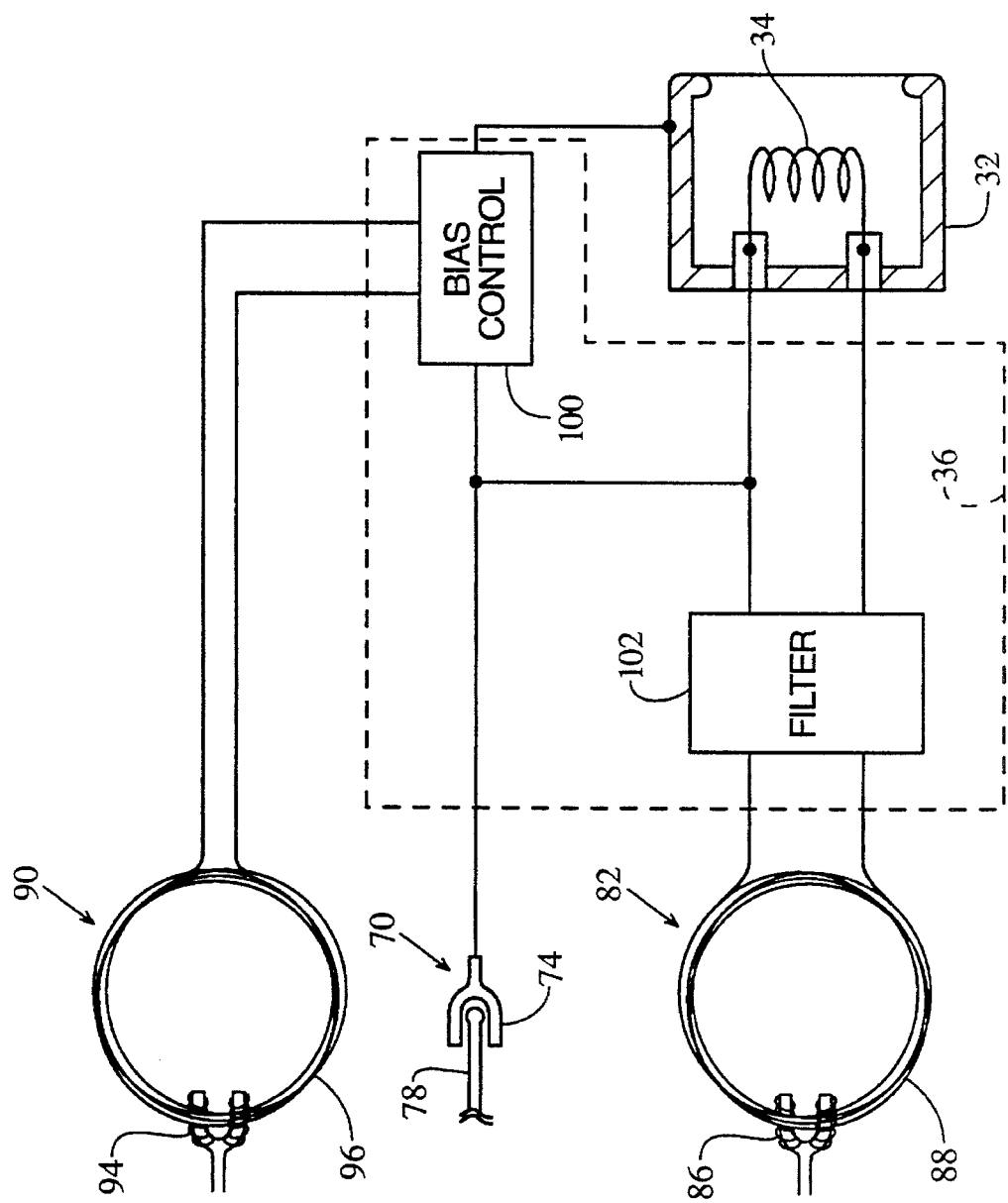
FIG. 3 is a circuit diagram of a circuit for adjusting and controlling potential bias of the cathode cup or a grid relative to the cathode filament.

With reference to FIG. 3 and continuing reference to FIG. 2, the cathode control circuit 36 connects the filament current from the secondary coil 88 of the second or filament power transfer means 82 to the filament 34. Optionally, the cathode control circuit may include a rectifier circuit for rectifying the filament current.

The cathode control circuit 36 also connects the bias potential from the hot filament 78 of the first or cathode electrical power transfer means 70 to the cathode filament 34. This causes the filament to be at about 150 kV negative, for example, relative to the anode.

The cathode control circuit 36 further includes a second bias control circuit 100 for biasing the cathode cup 32 relative to the filament 34 by the bias potential indicated by the first bias control circuit 92. Biasing the cup over a continuum of potentials relative to the filament controls the flow of electrons from the filament to the anode analogous to biasing potential on a grid. The bias on the potential cup relative to the filament is sometimes called a "grid bias".

For controlling which of the cathode assemblies are generating x-rays, a bandpass circuit 102 is connected between the secondary coil winding 88 and the filament. The bandpass frequency of the band pass circuit associated with each of the cathode assemblies is distinctly different. In this manner, by adjusting the frequency of the signal applied to the primary winding 86, the operator can select which bandpass circuit will pass the signal, hence which cathode filament will be heated.

Figure 4:
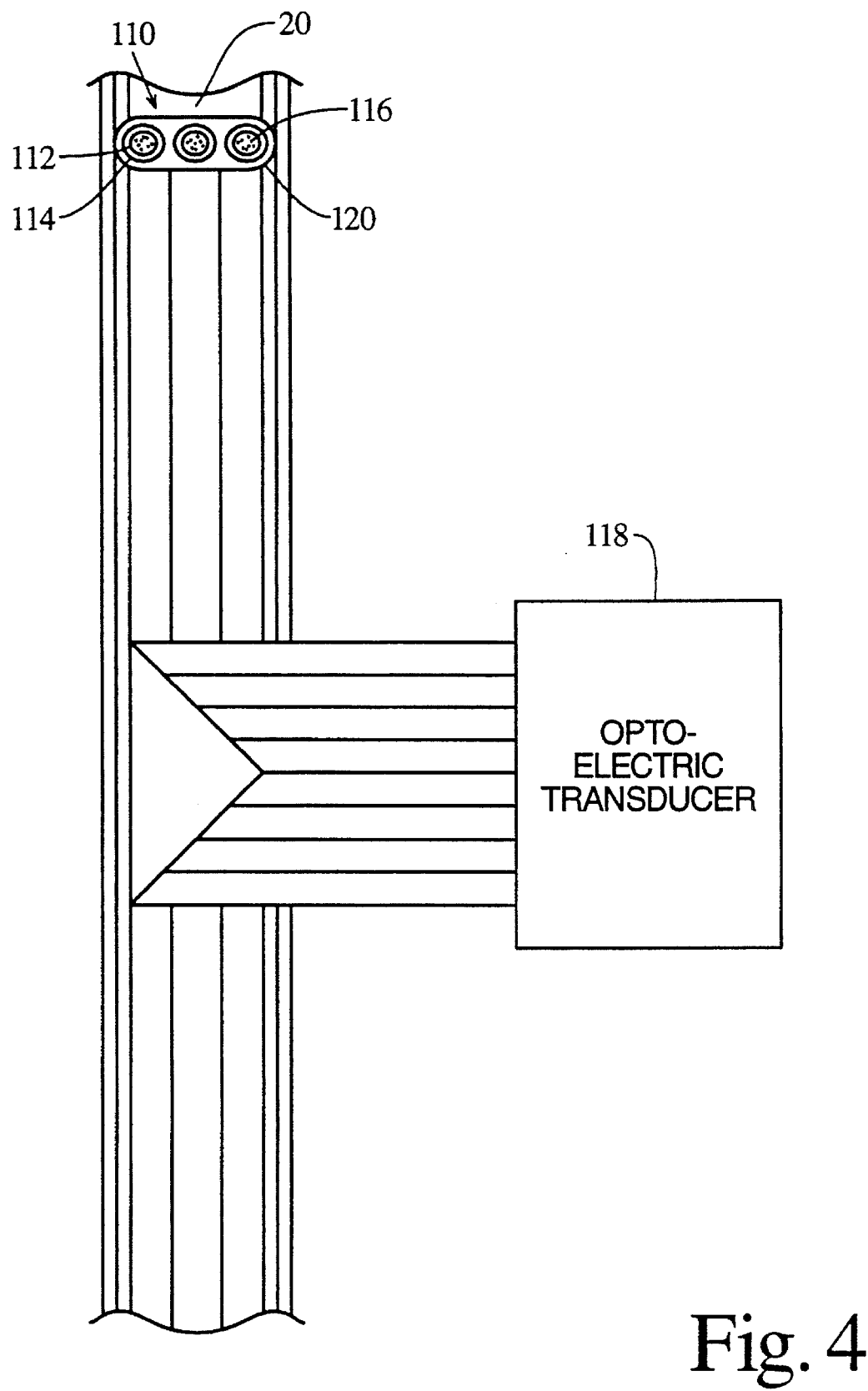
FIG. 4 is a detailed view of the scintillation fiber construction.

With particular reference to FIG. 4 and continuing reference to FIG. 2, a stationary radiation detector 110 is mounted across the window 20. More specifically to the preferred embodiment, the stationary radiation detector includes a band or stripe of scintillating optical fibers. In the embodiment of FIG. 4, three optical fibers with circular cross sections are shown for illustration purposes only. The preferred embodiment is composed of a ribbon of scintillating fibers with a total thickness of 1 mm or less. The individual fibers could be composed of round or square cross sections. Each of the fibers has an inner core 112 which is optically transmissive and an outer cladding 114. The relative indices of refraction of the inner core 112 and the outer sheathing 114 are such that light within the inner core that strikes the outer sheathing is reflected back into the inner core as in conventional optic fiber or light pipe. The inner core 112 includes fluorescent dopants 116 which convert x-rays into optical light of a characteristic wavelength. In this manner, when x-rays come through the window 20, the x-rays pass through the scintillation fibers causing the inner core to transform a small fraction of the x-rays into the light which is conveyed along the fibers to an opto-electrical transducer 118. Preferably, an optical sheathing 120 coats the fibers such that ambient light cannot enter the optical fibers creating erroneous readings or noise. In the illustrated embodiment, the scintillation fibers are folded back on themselves out of the window 20 and parallel to the central axis 24. In the preferred embodiment in which an annular radiation opaque shutter 122 is mounted slidably within the bore for selectively closing the window 20, the scintillating fibers pass between the window and the shutter.

With reference to FIGS. 1 and 3, the output of the opto-electrical transducer 118 is connected with a comparing means 124 which compares the amount of detected light, hence the intensity of the radiation, with a preselected radiation intensity from a selected radiation intensity memory 126. Based on the comparison, the comparing means 124 causes the first or grid bias control circuit 92 to increase or decrease the bias, hence the x-ray tube current, hence the x-ray intensity. It is to be appreciated that the selected intensity may be cathode angular position dependent as determined by the angular position of the patient. That is, the radiation intensity can be increased through the thicker dimension of the subject and decreased through the thinner dimensions. The selected intensity memory 126 may be in the form of a look-up table which is indexed or addressed by the rotation monitor 68 to retrieve the selected intensity corresponding to the current angular position of the apex of the x-ray beam.

The rotor also carries a collimator means, preferably a box collimator 130. Opposite side walls of the collimator box 130 in a direction parallel to the central axis control the width or thickness of the x-ray beam. Oppositely disposed walls of the collimator box 130 in the transverse direction control the fan angle of the x-ray beam. The collimator assembly also blocks any scattered x-rays from merging with the x-ray beam.

To maintain the vacuum within the vacuum region of the housing A, an active vacuum pumping means 140 is provided, e.g, an ion pump.

An annular ring of radiation detectors 160 is disposed around the interior of the bore 24. The detectors are disposed closely adjacent but slightly offset from the window 20. The detectors 160 produce signals which are indicative of radiation intensity received. The signals from the radiation detectors 160 and from the reference detector 110 mounted on the patient side of window 20 are connected to an intensity compensation circuit 162 which adjusts the detector signals in accordance with fluctuations in radiation intensity indicated by the output of the opto-electric transducer 118. The radiation intensity compensation function may also be performed by software in the reconstruction module. The intensity data is digitized and reconstructed by a volume image reconstruction means 164 into an image representation. The volume image representation is stored by volume image memory 166 from which selected information is withdrawn and converted into appropriate video format for display on a monitor 168.

Alternately, a plurality of discrete radiation detectors is disposed in a substantially uniform manner near the periphery of the exit beam. These discrete detectors are placed between the x-ray source and the annular slide collimator and are totally immersed in the incident x-ray beam and do not protrude into the defined slice. Since the thickness of the swath of x-rays incident on the annular slice collimator exceeds the width of the slice collimator, this condition is insured.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An x-ray tube comprising:
    a generally toroidal housing having an evacuated interior and an annular x-ray transmissive window;
    an annular anode mounted in the toroidal housing interior, the anode being in thermal communication with a circulated cooling fluid passage such that the cooling fluid removes heat from the anode;
    a rotor rotatably disposed within an interior of the toroidal housing;
    a plurality of cathode assemblies, each the cathode assembly selectively emitting electrons to form an electron beam that strikes the anode to generate an x-ray beam, the cathode assemblies being mounted to the rotor such that the electron beams rotate around the annular anode as the rotor rotates;
    a cathode assembly electrical power transfer circuit for transferring cathode assembly electrical power of a selectable frequency from the housing to the rotor;
    a plurality of bandpass circuits each having a different bandpass frequency, each of the bandpass circuits being connected between the cathode assembly electrical power transfer circuit and one of the cathode assemblies such that a one of the cathode assemblies to receive electrical power is selected by the frequency of the transferred electrical power.

2. An x-ray tube comprising:
    a generally toroidal housing having an evacuated interior and an annular x-ray transmissive window;
    an annular anode mounted in the toroidal housing interior, the anode being in thermal communication with a circulated cooling fluid passage such that the cooling fluid removes heat from the anode;
    a rotor rotatably disposed within an interior of the toroidal housing;
    at least one cathode assembly mounted to the rotor for rotation therewith, the cathode assembly including an electron source that emits electrons to form an electron beam that strikes the anode to generate an x-ray beam, such that the electron beam is rotated around the anode with the rotor;
    a scintillating optical fiber mounted adjacent the window such that radiation exiting the window passes through the scintillating optical fiber, the scintillating optical fiber converting a small amount of incident x-rays to optical light and transmitting the light therealong to provide an indication of radiation intensity.

3. The x-ray tube as set forth in claim 2 further including an opto-electrical transducer for converting the light conveyed through the scintillating optical fiber into an electrical radiation intensity signal.

4. The x-ray tube as set forth in claim 3 further including an electron beam adjusting means for controlling the electron beam to adjust an intensity of the generated x-ray beam.

5. The x-ray tube as set forth in claim 4 wherein the electron beam adjusting means includes:
    a biasing means disposed to provide an electric field between the cathode filament and a supporting filament cup; and,
    a means for adjusting the biasing means.

6. The x-ray tube as set forth in claim 5 wherein the bias adjusting means is mounted to the rotor for rotation therewith.

7. An x-ray tube comprising:
    a housing having an evacuated interior and a radiation transmissive window;
    an anode mounted in the housing;
    a cathode assembly mounted in the housing for generating an electron beam that strikes the anode causing x-rays to be generated and pass through the radiation transmissive window;
    a scintillating optical fiber mounted adjacent the radiation transmissive window for converting a fraction of incident x-rays to light and conveying the light therealong;
    an optical transducer which receives the light conveyed along the scintillating optic fiber and converts the received light into a radiation intensity reference signal.

8. A CT scanner comprising:
    a patient support for supporting a selected portion of a patient in an examination region;
    an x-ray ring tube including:
        a generally toroidal housing having an evacuated interior and an annular x-ray transmissive window;
        an annular anode mounted in the toroidal housing interior, the anode being in thermal communication with a circulated cooling fluid passage such that the cooling fluid removes heat from the anode;
        a rotor disposed within an interior of the toroidal housing;
        at least one cathode assembly mounted to the rotor for rotation therewith, the cathode assembly including an electron source which emits an electron beam that strikes the anode to generate an x-ray beam;
        the rotor being rotatably disposed in the housing such that electron beam is rotated around the anode;
    a scintillation optical fiber mounted adjacent the window such that x-rays exiting the window pass through the scintillating optical fiber, the scintillating optical fiber converting a small amount of incident x-rays to optical light and transmitting the light therealong;
    an opto-electric transducer which converts the light from the scintillating optical fiber into an x-ray intensity signal;

a gantry which supports and selectively positions the x-ray ring tube around the examination region;

a ring of radiation detectors for receiving x-rays from the window which have traversed the examination region;

an image reconstruction processor for reconstructing the signals from the ring of radiation detectors into image representations.

9. The CT scanner as set forth in claim 8 wherein the scintillating optical fiber extends annularly around an exterior of the x-ray transmissive window.

10. The CT scanner as set forth in claim 8 further including:

a comparator for comparing the x-ray intensity signal with a preselected radiation intensity;

a bias control circuit for adjusting a bias to a control assembly for the at least one cathode for adjusting the intensity of the generated x-ray beam in accordance with the comparison.

11. The CT scanner as set forth in claim 8 wherein the opto-electrical transducer is connected with the image reconstruction processor for adjusting image reconstruction for variations in x-ray intensity signals.

12. An x-ray tube comprising:

a generally toroidal housing having an evacuated interior and an an annular x-ray transmissive window;

an annular anode surface mounted in the toroidal housing interior;

a rotor rotatably disposed within an interior of the toroidal housing;

at least one cathode asssembly mounted to the rotor for rotation therewith, the cathode assembly including a filament which emits electrons to form an electron beam that strikes the anode to generate an x-ray beam;

a means for rotating the annular rotor such that electron beam is rotated around the anode surface;

a voltage biasing means disposed adjacent the cathode for establishing an electric field adjacent the cathode through which the electron beam passes to strike the anode;

a bias adjusting circuit for adjusting the electric field for adjustably controlling an intensity of the generated x-ray beam;

a first power transfer means for transferring a bias potential from the toroidal housing to the rotor to provide a potential to the cathode assembly relative to the anode;

a second electrical power transfer means for transferring a cathode filament current from the housing to the rotor for providing an electrical current for heating the filament of the cathode assembly;

a third electrical power transfer means for transferring power from the toroidal housing to the voltage biasing means.

13. The x-ray tube as set forth in claim 12 further including a plurality of cathode assemblies mounted to the rotor and further including a bandpass circuit connected between the cathod assembly and the second power transfer means, each of the bandpass circuits having a distinctly different bandpass frequency such that a frequency of the power transferred by the second power transfer means determines which cathode assembly receives the filament current.

14. An x-ray tube comprising:

a generally toroidal housing having an evacuated interior and an annular x-ray transmissive window;

an annular anode surface mounted in the toroidal housing interior, the anode being in thermal communication with a circulated cooling fluid passage such that the cooling fluid removes heat from the anode;

a rotor rotatably disposed within an interior of the toroidal housing;

at least one cathode assembly mounted to the rotor for rotation therewith, the cathode assembly including an electron source that emits an electron beam that strikes the anode to generate an x-ray beam such that electron beam is rotated around the anode surface as the rotor rotates;

a voltage biasing element disposed adjacent the cathode for establishing an electric field adjacent the cathode through which the electron beam passes to strike the anode;

a bias adjusting circuit for adjusting the electric field over a continuum of strengths for adjustably controlling the electron beam over a continuum of magnitudes for adjustably controlling an intensity of the generated x-ray beam over a continuum of intensities.

15. The x-ray tube as set forth in claim 14 further including an x-ray intensity sensor disposed along a linear path defined by the anode and the window, the x-ray intensity sensor being connected with the bias adjusting circuit for providing an indication of actual x-ray beam intensity thereto.

16. The x-ray tube as set forth in claim 15 wherein the x-ray intensity sensing means includes a scintillating optical fiber.

17. The x-ray tube as set forth in claim 15 further including a comparator for comparing the x-ray intensity from the x-ray intensity sensor with a preselected x-ray intensity, the bias adjusting circuit being connected with the comparator for adjusting the electric field in accordance with a deviation between the sensed and preselected x-ray intensities.

18. A CT scanner comprising:

a patient support for supporting a selected portion of a patient in an examination region;

an x-ray ring tube including:
 a generally toroidal housing having an evacuated interior and an annular x-ray transmissive window;
 an annular anode mounted in the toroidal housing interior, the anode being in thermal communication with a circulated cooling fluid passage such that the cooling fluid removes heat from the anode;
 a rotor rotatably disposed within an interior of the toroidal housing;
 at least one cathode assembly mounted to the rotor for rotation therewith, the cathode assembly including a means for emitting electrons to form an electron beam that strikes the anode to generate an x-ray beam;
 a transformer for supplying electrical power to the cathode assembly, the transformer including an annular winding extending around and mounted to the rotor for rotation therewith and a U-shaped winding mounted to the housing and receiving the annular winding therethrough;
 a means for rotating the annular rotor such that electron beam is rotated around the anode and such that the annular winding moves through the U-shaped winding;
 a radiation intensity monitoring means mounted adjacent the window such that x-rays exiting the window pass through the radiation intensity monitoring means;
a gantry which supports and selectively positions the x-ray ring tube around the examination region;
a ring of radiation detectors for receiving x-rays from the window which have traversed the examination region;
an image reconstruction means for reconstructing signals from the ring of radiation detectors into image representations.

19. The CT scanner as set forth in claim 18 further including a cathode control means for controlling the electron beam to adjust an intensity of the generated x-ray beam in accordance with monitored variations in radiation intensity.

20. The CT scanner as set forth in claim 19 wherein the cathode control means includes:
a biasing means disposed between the cathode and the anode for providing an adjustable voltage bias which adjustably restricts the electron beam that strikes the anode; and,
a bias adjusting means for adjusting the voltage bias.

21. An x-ray tube comprising:
a generally toroidal housing having an evacuated interior and an annular x-ray transmissive window;
an annular anode surface mounted in the toroidal housing interior, the anode being in thermal communication with a circulated cooling fluid passage such that the cooling fluid removes heat from the anode;
a rotor rotatably disposed within an interior of the toroidal housing;
at least one cathode assembly mounted to the rotor for rotation therewith, the cathode assembly including an electron source which forms an electron beam that strikes the anode to generate an x-ray beam such that electron beam is rotated around the anode surface;
a voltage biasing structure disposed adjacent the cathode for establishing an electric field adjacent the cathode through which the electron beam passes to strike the anode;
a bias adjusting circuit for adjustably controlling the electron beam to control an intensity of the x-ray beam which passes through the electric field and strikes the anode, the bias adjusting circuit being mounted on the rotor within the evacuated interior of the toroidal housing, the bias adjusting circuit being sealed in a vacuum tight container which is mounted to the rotor for rotation therewith.

22. A CT scanner comprising:
a patient support for supporting a selected portion of a patient in an examination region;
an x-ray ring tube including:
a generally toroidal housing having an evacuated interior and an annular x-ray transmissive window;
an annular anode mounted in the toroidal housing interior, the anode being in thermal communication with a circulated cooling fluid passage such that the cooling fluid removes heat from the anode;
a rotor rotatably disposed within an interior of the toroidal housing;
at least one cathode assembly mounted to the rotor for rotation therewith, the cathode assembly including an electron emitting source which forms an electron beam that strikes the anode to generate an x-ray beam such that electron beam is rotated around the anode;
a voltage biasing means for creating a bias voltage field between the cathode assembly and the anode such that the electron beam passes therethrough;
a bias adjusting circuit for adjustably modulating the bias voltage field over a multiplicity of field strengths for adjustably controlling an intensity of the generated x-ray beam over a multiplicity of x-ray beam intensities;
a gantry which supports and selectively positions the x-ray ring tube around the examination region;
a ring of radiation detectors for receiving radiation from the x-ray ring tube which have traversed the examination region;
an image reconstruction processor which reconstructs signals from the radiation detector ring into image representations.

23. The CT scanner as set forth in claim 22 further including:
an electrical power transfer means for transferring a bias voltage field across the vacuum between the toroidal housing and the rotor.

24. The CT scanner as set forth in claim 22 further including:
a scintillation optical fiber disposed along the x-ray transmissive window for generating a light signal indicative of an intensity of radiation passing therethrough;
an opto-electrical transducer for converting the light signal to an electrical x-ray intensity signal, the opto-electrical transducer being connected with the bias adjusting circuit.

25. The x-ray tube as set forth in claim 22 further including a plurality of cathode assemblies mounted to the rotor and further including a bandpass circuit connected with each cathode assembly, each of the bandpass circuits having a distinctly different bandpass frequency such that the frequency of cathode power transferred to the rotor determines which cathode assembly is activated.

* * * * *